United States Patent [19]

Cordner, Jr. et al.

[11] Patent Number: 5,244,463
[45] Date of Patent: Sep. 14, 1993

[54] PROGRAMMABLE INFUSION PUMP

[75] Inventors: Edward T. Cordner, Jr., Oceanside; George T. Walker, III, San Diego; Howard S. Barr, Escondido; Farid Khadem, San Diego, all of Calif.

[73] Assignee: Block Medical, Inc., Carlsbad, Calif.

[21] Appl. No.: 804,828

[22] Filed: Dec. 6, 1991

[51] Int. Cl.⁵ .................................... A61M 37/00
[52] U.S. Cl. ................................ 604/131; 604/67; 604/132; 604/151; 128/DIG. 12
[58] Field of Search ............... 128/DIG. 12; 604/65, 604/67, 131, 132, 151, 152, 153, 154

[56] References Cited

U.S. PATENT DOCUMENTS

| | | | |
|---|---|---|---|
| 4,335,835 | 6/1982 | Beigler et al. | 604/131 |
| 4,430,078 | 2/1984 | Sprague | 604/118 |
| 4,525,165 | 6/1985 | Fischell | 604/131 |
| 4,559,038 | 12/1985 | Berg et al. | 604/153 |
| 4,565,542 | 1/1986 | Berg | 604/131 |
| 4,650,946 | 3/1987 | Berg et al. | 604/131 |
| 5,078,683 | 1/1992 | Sancoff et al. | 604/31 |

Primary Examiner—Randall L. Green
Assistant Examiner—Paul Prebilic
Attorney, Agent, or Firm—Baker, Maxham, Jester & Meador

[57] ABSTRACT

An infusion pump system, comprises disposable tubing having an elastic segment and one-way check valves at each end of the segment for conveying intravenous fluid from a source to a patient, a compact, portable housing having an open receptacle for removably receiving a segment of the disposable tubing, a reciprocating ram mounted in the housing for periodically engaging and compressing the segment of the disposable tubing for pumping fluid therethrough, a motor mounted in the housing for driving the ram upon energization thereof, a control system mounted in the housing for receiving input signals and energizing the motor so that the fluid is pumped through the disposable tubing in accordance with pre-selected delivery rate parameters.

21 Claims, 3 Drawing Sheets

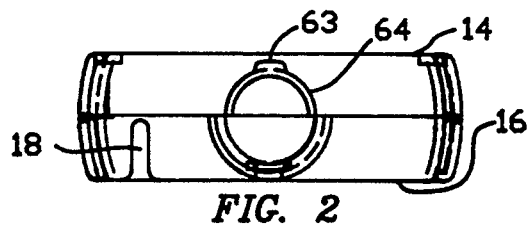
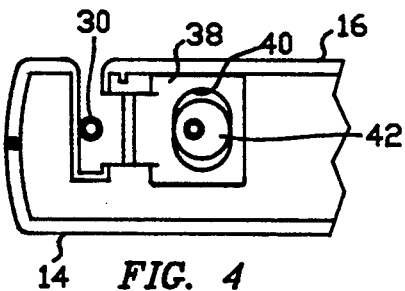
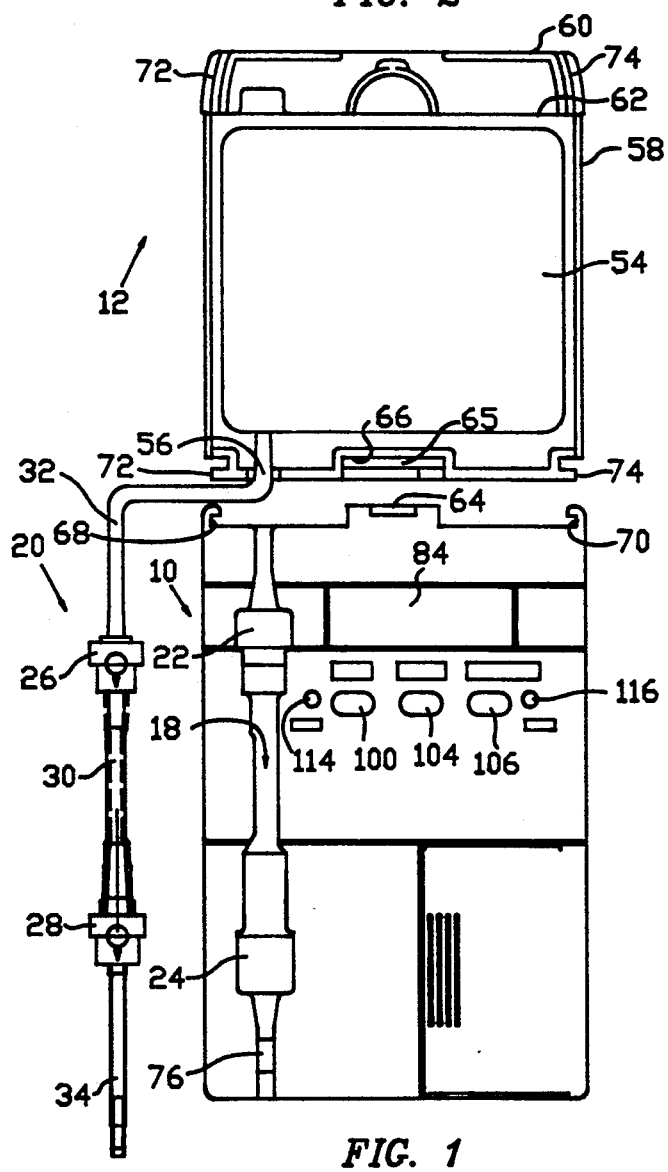
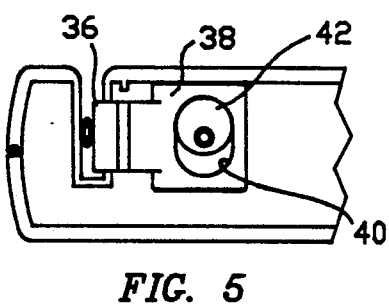
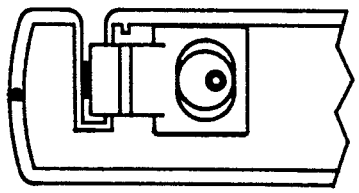

PROGRAMMABLE INFUSION PUMP

BACKGROUND OF THE INVENTION

The present invention relates to medical devices, and more particularly, to an improved programmable infusion pump for delivering intravenous drugs at a controlled rate to a patient.

It is often necessary to intravenously supply patients with pharmaceutically active liquids over a long period of time at a controlled rate. It is desirable that this be accomplished while the patient is in an ambulatory state.

The prior art includes devices that employ a bag filled with fluid medication that feeds by gravity through IV tubing having drip or other controllers. It is difficult for a patient to be ambulatory with a gravity fed infusion device. In addition, flow control in this type of device is very limited.

Another prior art infusion apparatus comprises an elastic bladder forming a liquid container, an elongated cylindrical housing enclosing the bladder, a flow control valve, and tubing for supply of the liquid to the patient. The elastic walls of the bladder expand along the walls of the cylindrical housing when filled with the liquid, and provide the pressure for expelling the liquid. The bladder is typically filled by hand with a syringe which often requires an inordinate amount of force. Another drawback is that the bladder is forced to expand into an unnatural elongated configuration along the housing walls as it is filled. As a result of this unnatural configuration, the pressure of the bladder varies widely with the volume of liquid therein. Therefore, in most cases, this type of elastic infusion apparatus does not have a reasonably stable pressure and flow rate over the infusion period. Most of such devices either have a flow rate that decreases with pressure, which decreases with volume, or one that remains roughly constant until the end where it surges. Attempts have been made to control pressure and flow rates by means of complicated and expensive flow control valves and devices. Other approaches have utilized exotic and expensive elastic materials in an effort to control the pressures and flow rates.

Another type of infusion apparatus uses pressurized gas as the driving force for the intravenous liquid. In such systems there may be hydraulic feedback through the pneumatic source in order to precisely regulate hydraulic pressure. See for example U.S. Pat. Nos. 4,430,078 of Sprague, 4,335,835 of Beigler et al., and 4,327,724 of Birk et al. Such pneumatically driven infusion devices tend to have reducing flow rates and pressures as the stored pressurized gas source is exhausted.

Still another type of infusion apparatus employs a peristaltic or other positive displacement pump which is electrically driven. Programmable infusion pumps have been provided having the capability for precise tailoring of the fluid delivery rate parameters in different modes, such as, continuous, intermittent, PCA (patient controlled analgesic) and TPN (total parenteral nutrition). Originally, such programmable infusion pumps were large and not well suited for ambulatory patients. They used complex and expensive replacement pump cartridges to maintain sterility.

More recently, small programmable infusion pumps have been available with disposable plastic cartridges that engage a peristaltic pump. However, such cartridges have been bulky and expensive and have required excessive drive power in the pumps, leading to rapid battery drain. Another drawback of these existing programmable infusion systems of this type is that they are complicated and very expensive to manufacture and to maintain.

There is an ever increasing desire in the health care field to get patients out of expensive hospital care environments and back to their homes. Many such patients require intravenously administered medications, but are unable to program existing programmable infusion systems themselves, and trained operators cannot economically visit their homes. In addition, many such patients are unable to change the delivery rates in accordance with subsequent physician prescriptions. Furthermore, they cannot effectively verify the prescribed delivery parameters.

Accordingly, it would be desirable to provide an improved low cost single channel programmable infusion system for delivering intravenous drugs at a controlled rate to an ambulatory patient that can be more easily programmed by a patient, and which will allow patient verification of the prescribed delivery parameters.

SUMMARY OF THE INVENTION

It is, therefore, the primary object of the present invention to provide an improved low cost programmable infusion pump for an ambulatory patient, which enables intravenous fluid delivery parameters to be readily programmed and verified by the patent.

Our invention comprises a programmable infusion system, which includes a disposable IV tubing apparatus for conveying intravenous fluid from a source to a patient. The system further includes a compact, portable housing having a receptacle slot for removably receiving a segment of the disposable tubing. A fixed stroke pump is mounted in the case for engaging the segment of the disposable apparatus and pumping intravenous fluid therethrough. A motor is mounted in the housing and is connected for driving the pump upon energization thereof. A keyboard includes a rate key for selecting the infusion rate and a volume key for selecting the volume. The tubing is attached to the source of intravenous fluid, such as a bag. A display is mounted in the housing for visually displaying information in alphanumeric form. A microcontroller mounted in the housing receives the input signals and causes the display to provide a visual indication of the delivery rate parameters in alphanumeric form for selection and verification by the patient. The microcontroller energizes the motor so that the expansion chamber pump conveys the fluid through the disposable apparatus in accordance with the delivery rate parameters.

In the illustrated embodiment of our invention, the system includes a keypad mounted in the housing for enabling the user to send commands to the microcontroller. A detector mounted in the housing optically detects the presence of a bubble inside the segment of the disposable tubing and sends a bubble detect signal to the micro-controller.

The preferred embodiment of our programmable infusion system has the capability for detecting an interrupt condition, such as the failure to load a disposable apparatus therein, an occlusion in the disposable apparatus, a motor failure, a pump failure, or a bubble in the disposable apparatus. The microcontroller can then de-energize the motor in response to the detection of an interrupt condition, and cause the display means to display a warning of the interrupt condition in alphanumeric form. It can also cause an audible warning to be generated, such as a succession of beep tones, and a visible warning to be given in the form of an illuminated red LED.

BRIEF DESCRIPTION OF THE DRAWINGS

The above and other objects and advantages of the present invention will become apparent from the following description when read in conjunction with the accompanying drawings wherein:

FIG. 1 is a front elevation view of a preferred embodiment of the invention showing the main and reservoir housings;

FIG. 2 is a top view of the main housing detached;

FIGS. 4-6 are like views in section taken on line 4—4 of FIG. 3 showing the pump in different stages of its stroke;

DESCRIPTION OF THE PREFERRED EMBODIMENT

Figure 3:
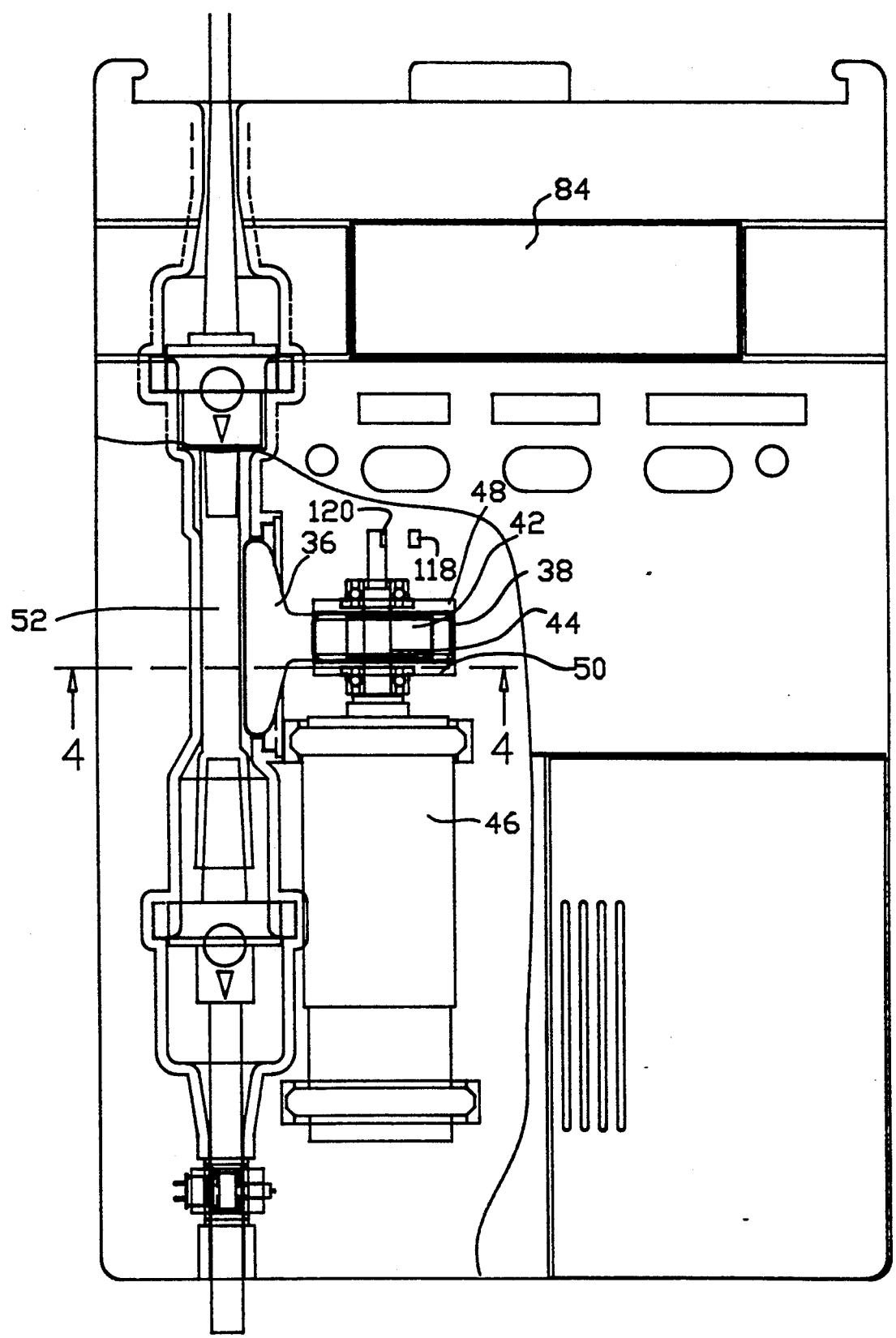
FIG. 3 is a partial view like FIG. 1, with portions broken away to reveal details.

Referring to FIG. 1 of the drawings, there is illustrated in an exploded view an exemplary preferred embodiment of the invention. The illustrated embodiment comprises a main or central housing, designated generally by the numeral 10, and a detachable reservoir housing, designated generally by the numeral 12. The main housing 10 houses the pump drive and actuating mechanism, as will be more fully described with respect to FIGS. 2 and 3-5, and the control means for the pump system. The control means comprises electronics for driving and controlling the drive of the pump unit for indicating various parameters and the like.

Referring to FIGS. 1 and 2, the main housing is of a generally box-like configuration formed of front and back half-shells 14 and 16. The face or face panel 16 is formed with an open slot 18 extending from the top to the bottom of the panel, and is open to the face thereof for receiving a disposable unit 20 comprising a portion of the pump unit. This slot communicates at the upper end, with the reservoir housing 12 to receive tubing extending therefrom. The slot is formed with smaller width portions at the upper inlet end and the lower outlet end for receiving conventional IV tubing. Enlarged sections 22 and 24 are designed to receive valve units 26 and 28 which are connected in fluid communication by an elastic tube member 30.

The disposable unit 20, as illustrated in FIG. 1, comprises said elastic tube member 30 of a selected length, diameter and bore size connected between said inlet valve 26 and said outlet valve 28, each of which are respectively connected to an IV supply line 32 and an IV delivery line 34. There is, therefore, a complete fluid path from supply line 32, through inlet valve 26, through elastic tube member 30, through outlet valve 28, and through IV delivery line 34. The elastic tube member 30 is preferably an elastomeric silicone, but may be any other suitable medical grade synthetic or natural rubber of between about fifty and seventy durometers on the Shore A scale. The member 30 must having sufficient elasticity to restore itself rapidly after being compressed sufficiently to provide the upper limits of volume to be pumped.

The member 30 for this configuration is selected to have a 0.100 inches ID and 0.160 inches OD, with an overall length of 1.5 inches and a length between the valves 26 and 28 of about 0.875. This gives a volume to assure self priming of the pump with the given check valves 26 and 28.

The check valves 26 and 28 comprise a substantially zero cracking pressure inlet check valve 26, which is preferably a duckbill type, which may have a cracking pressure of up to about 0.5 psi. The outlet valve 28 is preferably a 2 to 6 psi disc spring type.

The actuating mechanism of the pump unit, as best seen in FIGS. 3-6, comprises a ram or finger member comprising a foot member 36 mounted on the lower end of a reciprocating plunger unit 38, having a slot or yoke 40 therein in which an eccentric cam member 42 rotates. The eccentric cam unit 42 is mounted on the end of a motor driven shaft 44, which is driven by means of a DC electric motor 46 disposed within the housing. The motor 46 is preferably powered by either a lithium or alkaline 9 volt battery. The finger or slide member 38 is disposed between and guided by guide or wall members 48 and 50 within the housing.

The foot member 36 preferably has substantially the same length along the slot 18 as the member 30, so as to compress the member 30 to essentially zero internal volume. The member 30 is pressed between the foot member 36 and a stationary platen 52 on the opposite side of the slot 18.

The pump mechanism functions similar to any expansion chamber type pump, with the collapsing and expansion of the member 30 forming an expansion chamber pump. The unit becomes self-priming by virtue of the selection of parameters to provide for creation of sufficient pressure, with air therein to open the outlet check valve 28 and forces movement of the column of air therethrough. This follows the principal of Boyles Law wherein $P' \times V' = P'' \times V''$.

Referring back to FIG. 1, the unit in its preferred embodiment pumps fluid from a reservoir 54 contained within the reservoir housing 12. The reservoir 54 is preferably of a conventional construction of one-hundred milliliter volume bag made of PVC film and is disposable. The line 32 can be integrated with the original reservoir 54, or a connection luer lock can be used to connect the line 32 to a larger volume reservoir of infusion fluid. The reservoir housing 12 is of a box-like construction of opposed half-shells 58 and 60, shown in the illustrated embodiment as hinged together along a hinge connection 62, with the front panel 60 shown open. The reservoir housing 12 is constructed to detachably connect to the upper end of the main housing 10 by means of a bayonette type coupling. As illustrated, the upper end of the housing 10 is formed with central upwardly extending cylindrical pilot member 64, which extends into a cylindrical recess 66 in the bottom end of the reservoir housing 12. Radially extending tabs 63 on member 64 extend into annular slots 65 in the wall of recess 66. A pair of arcuate slots 68 and 70 formed in the upper end of the main housing 10 receive a pair of radially extending arcuate flanges 72 and 74 formed on the housing 12. Thus, to attach or detach the housing 12 from the upper end of the main housing 10, the reservoir housing 12 is axially aligned along the members 64 and 66, and rotated about the axis to alternately engage or disengage the flanges 72 and 74 with the arcuate slots 68 and 70. When the reservoir housing 12 is disengaged and detached from the main housing 10, it may be opened as illustrated, and the reservoir 54 either removed or replaced therein.

The control system for the present invention has some common features and components of co-pending application Ser. No. 07/518,987, filed May 4, 1990 now U.S. Pat. No. 5,078,683 dated Jan. 7, 1992, entitled "Programmable Infusion System", and assigned to the assignee herein, said application for which the issue fee was been paid on Oct. 17, 1991, is incorporated herein by reference as though fully set forth. The present invention, for example, incorporates an air in line (or bubble) detector, as disclosed in the aforementioned application. It may also include or incorporate an occlusion detector similar to that as set forth. However, an alternate detector system as will be sequentially explained is preferred.

Figure 7:
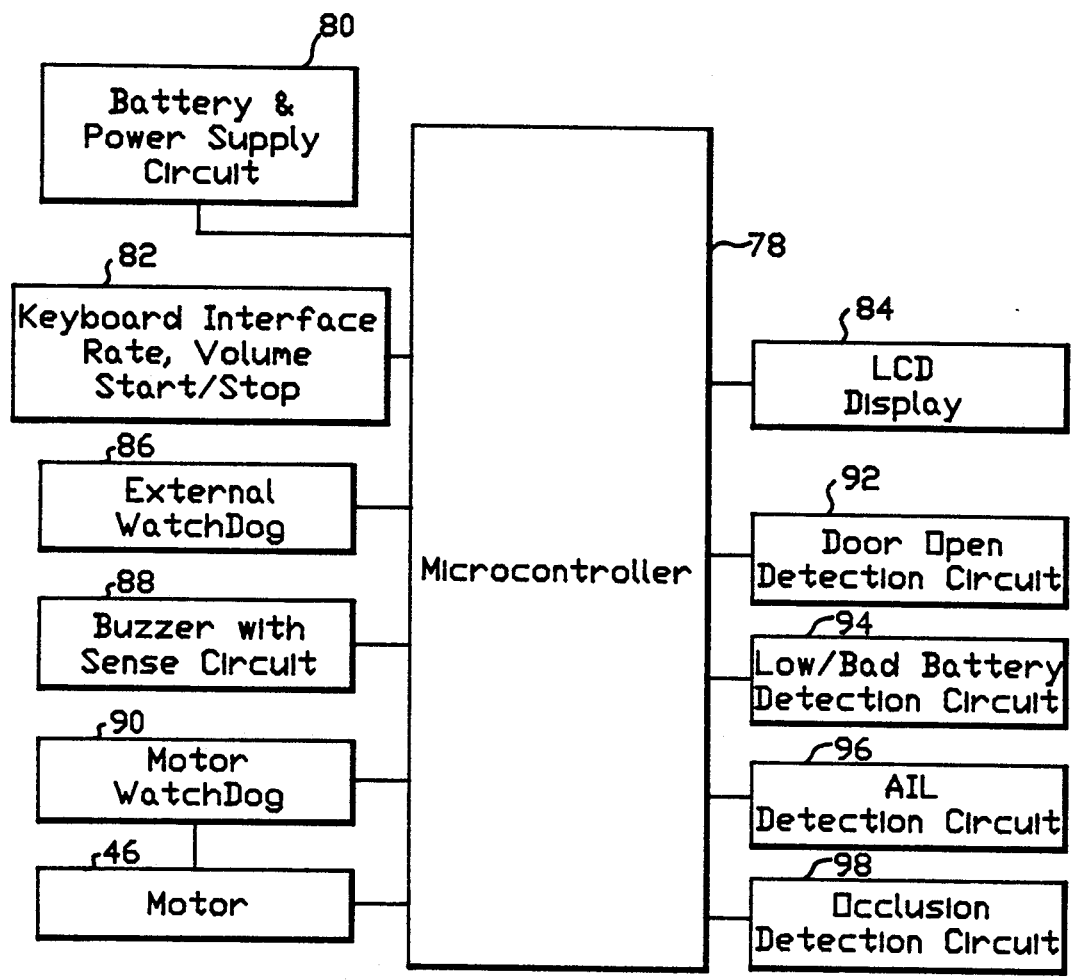
FIG. 7 is a block diagram of the control system of the embodiment of FIG. 1.
Figure 8:
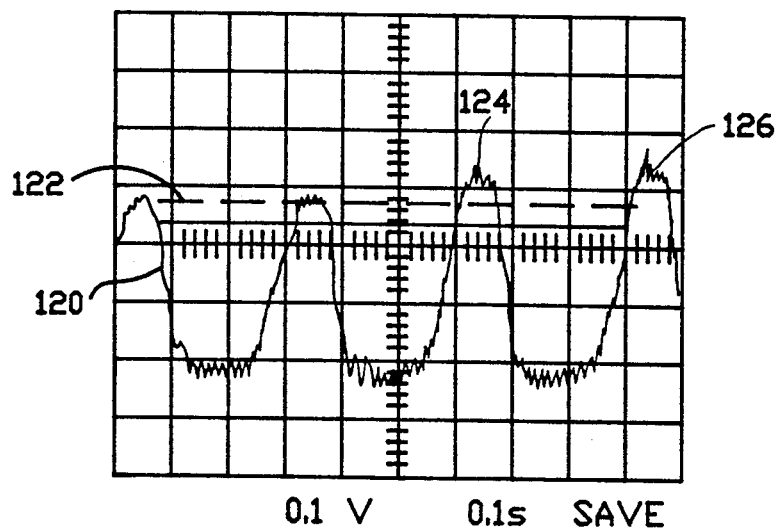
FIG. 8 is a graph illustrating motor load under occluded and non-occluded conditions.

Referring to FIG. 7, a block diagram of the control system is illustrated. The heart of the control system is a microcontroller 78, with user interface in the form of a keyboard on the face 16 of the unit, with motor control for controlling flow and various fault analysis. The system has the usual battery and power supply circuit 80 connected to power the overall system, with a keyboard interface 82 to enable an operator input to the microcontroller for control or selection of rate, volume, and to start and stop the unit. A LCD display 84 displays information to the user relative to operational parameters, including rate, volume, start and stop, and conditions of the unit. A number of monitoring and sensing functions, including external watchdog 86, signals the microcontroller, which in turn signals the user by audible means, such as a buzzer 88. Among the sensing functions are also a motor watchdog 90 monitoring the motor 46, which in turn is controlled by the microcontroller. Other sensors include a door open detection circuit 92 to detect the absence of tube 30 from slot 18, a battery condition detection circuit 94, air in line detection circuit 96 and an occlusion detection circuit 98. The control means includes means for detecting an interrupt condition from the group consisting of disposable means not loaded, occlusion in the disposable means, failure in the motor means, failure in the pump means, and bubble in the elastic segment of the disposable means, for de-energizing the motor means in response thereto and for causing the display means to display a warning of the interrupt condition in alphanumeric form.

The presence of an occlusion in the system, that is an obstruction that stops or substantially slows fluid flow, may be measured as a function of current used by the motor 46, a function of the speed of rotation of the motor 46, or a combined function of these two factors. The occlusion detection circuit 98 measures the current used by the motor 46 during the pumping stroke and also through the use of a hull effect shaft encoder 118, which senses mounting of a magnet 120 carried by the shaft 44 of the motor 46. An occlusion will cause either a variation in the current used by the motor 46 or a variation in the rotational speed of the shaft 44 or, in some cases, both variations will occur. The occlusion detection circuit 98 monitors these factors and presents data to the microcontroller 78 for decision making and generation of an error signal when the pressure of an occlusion is determined.

The microcontroller 78 is preferably a Motorola MC68HC711E9. The microcontroller 78 will be preprogrammed for all operational parameters, with the exception of specific volume and rate of delivery, which may be selected by the operator from the control panel. The operator controls infusion rates from the keyboard interface 82 with a rate control key 100, which may set the rate of delivery or infusion rate by pressing down the key until the rate desired is indicated by the LCD display. The infusion rates will be displayed at LCD 84 and consists of ten discrete steps between 25 and 250 millimeters/hr. in 25 millimeter/hr. increments. This key also allows the user to enable or disable the air in line detector circuit 96 and also to prime the unit before an infusion is started.

A volume key 104 is operational to set the infusion volume the same as above, with for example twelve infusion volumes chosen, arranging from fifty to three-thousand millimeters, with volumes for example fifty, one-hundred, two-hundred fifty, fifty, five-hundred, six-hundred, one-thousand, twelve-hundred, fifteen-hundred, eighteen hundred, two-thousand, twenty-four hundred and three-thousand. The volume is also indicated by LCD 84. A start and stop key 108 initiates the infusion and enables the user to stop the priming of the unit.

The LCD display 84 is divided into four quadrants, with the rate of infusion shown in the upper left, the volume selected in the upper right, and the volume actually infused at any time in the lower right. User messages will be displayed in the lower left which notify the user of the pump status, alarm conditions or pump errors. All of the alarm conditions previously mentioned will notify the user by message on the LCD display 84. In the preferred mode, alarm messages may be accompanied by an intermittent or constant audible tone, together with a red LED alarm. A fault LED alarm indicator may be provided at 114 in the form of a red LED. A run indicator 116 is provided in the form of a green LED.

In operation, an infusion unit is selected and loaded with the reservoir 54 of IV solution, with tubing 32 and 34 and disposable unit 20 attached thereto. The disposable IV reservoir 54 is mounted within the solution reservoir housing 12, and the housing 12 attached to the upper end of the housing 10, with the disposable tubing segment 30 placed in the receptacle slot 18 clipped or retained therein by any suitable means. Preferably, there is a snap fit between the check valves 26 and 28 and the enlarged sections 22 and 24 of the slot 18. The pump is primed and the delivery tube 34 is then connected to the patient infusion site in the normal manner, and the unit is activated to set the infusion rate and volume. Once the rate and volume has been set, the unit is then activated and allowed to run its normal rate to infuse the selected volume of IV solution. Once the volume has been reached, the machine will stop operation and may then be disconnected.

While we have illustrated and described our invention by means of a specific embodiment, it should be understood that numerous changes and modifications may be made therein without departing from the spirit and scope of the invention as defined in the appended claims. We further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by us for carrying out the invention.

Therefore, the protection afforded our invention should only be limited in accordance with the scope of the following claims.

We claim:

1. An infusion pump system, comprising:
   disposable tubing means having an elastic segment and one-way check valves at each end of said segment, said valves oriented in a common direction thereby defining an inlet valve and an outlet valve, and said inlet valve has a lower cracking pressure than said outlet valve for conveying intravenous fluid from a source to a patient;
   a compact, portable housing having an open receptacle for removably receiving said elastic segment and said check valves of the disposable tubing means;
   reciprocating ram means mounted in the housing for periodically engaging and compressing the segment of the disposable tubing means for pumping fluid therethrough;
   motor means mounted in the housing for driving the ram means upon energization thereof; and
   control means mounted in the housing for energizing the motor means so that the fluid is pumped through the disposable means in accordance with pre-selected delivery rate parameters.

2. An infusion pump system according to claim 1 wherein said inlet valve has substantially zero cracking pressure.

3. An infusion pump system according to claim 1 wherein said elastic segment has a durometer of between 50 and 70 on the Shore A scale.

4. An infusion pump system according to claim 1 wherein said ram has a foot extending substantially the full length of said elastic segment.

5. An infusion pump system according to claim 1 and further comprising reservoir means including detachable housing means for containing a disposable bag for containing an intravenous solution.

6. An infusion pump system according to claim 1 wherein said check valves are oriented in a common direction thereby defining an inlet valve and an outlet valve, said inlet valve has substantially zero cracking pressure and said outlet valve has a cracking pressure of between two and five psi.

7. An infusion pump system according to claim 6 wherein said ram has a foot extending substantially the full length of said elastic segment.

8. An infusion pump system according to claim 7 wherein said elastic segment has a durometer of between 50 and 70 on the Shore A scale.

9. An infusion pump system according to claim 8 and further comprising reservoir means including detachable housing means for containing a disposable bag for containing an intravenous solution for connection to said disposable tubing means.

10. An infusion pump system according to claim 8 wherein said control means includes means for controlling the rate of flow and means for controlling the volume of flow.

11. An infusion pump system according to claim 1 and further comprising means mounted in the housing for generating an audible warning signal in the event of system interrupt condition.

12. A programmable infusion pump system, comprising:
    disposable tubing means having an elastic segment and an inlet check valve at one end of said elastic segment and an outlet check valve at the other end of said elastic segment for conveying intravenous fluid from a source to a patient, said inlet check valve having a lower cracking pressure than said outlet check valve;
    a compact, portable housing having an open receptacle for removably receiving said elastic segment of the disposable tubing means;
    reciprocating ram means mounted in said housing for periodically engaging and compressing the elastic segment of the disposable tubing means for pumping fluid therethrough;
    motor means mounted in the housing for driving the ram means upon energization thereof; and
    control means mounted in the housing for receiving input signals for energizing the motor means so that fluid is pumped through the disposable tubing means in accordance with pre-selected delivery rate parameters.

13. A programmable infusion pump system according to claim 12 wherein said ram has a foot extending substantially the full length of said elastic segment.

14. A programmable infusion pump system according to claim 13 wherein said elastic segment has a durometer of between 50 and 70 on the Shore A scale.

15. A programmable infusion pump system according to claim 14 and further comprising reservoir means including detachable housing means for containing a disposable bag for containing an intravenous solution.

16. A programmable infusion pump system according to claim 15 wherein said control means includes means for controlling the rate of flow and means for controlling the volume of flow.

17. A programmable infusion pump system according to claim 16 and further comprising means mounted in the housing for generating an audible warning signal in the event of system interrupt condition.

18. An infusion pump system according to claim 1 and further comprising keypad means mounted in the housing for enabling the user to send commands to the control means.

19. A programmable infusion pump system according to claim 17 and further comprising means for detecting a bubble inside the disposable means and for sending a bubble detect signal to the control means.

20. A programmable infusion pump system according to claim 17 wherein the control means includes means for detecting an interrupt condition from the group consisting of disposable means not loaded, occlusion in the disposable means, failure in the motor means, failure in the pump means, and bubble in the elastic segment of the disposable means, for de-energizing the motor means in response thereto and for causing the display means to display a warning of the interrupt condition in alphanumeric form.

21. A programmable infusion pump system according to claim 20 and further comprising means mounted in the housing for generating an audible warning signal in response to the control means detecting an interrupt condition.

* * * * *